(12) United States Patent
Fischer et al.

(10) Patent No.: US 8,833,145 B2
(45) Date of Patent: Sep. 16, 2014

(54) METHOD AND DEVICE FOR DETERMINING THE SOOT CONCENTRATION IN THE ENGINE OIL OF INTERNAL COMBUSTION ENGINES

(75) Inventors: Felix Fischer, Nürnberg (DE); Harald Beck, Nürnberg (DE)

(73) Assignee: MAN Truck & Bus AG, Munich (DE)

( * ) Notice: Subject to any disclaimer, the term of this patent is extended or adjusted under 35 U.S.C. 154(b) by 287 days.

(21) Appl. No.: 13/274,733

(22) Filed: Oct. 17, 2011

(65) Prior Publication Data

US 2012/0090386 A1    Apr. 19, 2012

(30) Foreign Application Priority Data

Oct. 16, 2010  (DE) .......................... 10 2010 048 748

(51) Int. Cl.
*G01N 15/00* (2006.01)
*G01N 21/00* (2006.01)
*G01M 15/00* (2006.01)

(52) U.S. Cl.
USPC ........................ 73/61.71; 73/23.33; 73/114.71

(58) Field of Classification Search
USPC ............ 73/61.41, 61.71, 61.73, 61.74, 23.33, 73/114.71, 53.05, 23.31
See application file for complete search history.

(56) References Cited

U.S. PATENT DOCUMENTS

| 4,281,533 A | 8/1981 | Eesley et al. |
| 4,345,202 A * | 8/1982 | Nagy et al. ..................... 324/642 |
| 4,567,750 A * | 2/1986 | Artmann ....................... 73/23.33 |
| 4,780,832 A * | 10/1988 | Shah ............................. 702/130 |
| 5,009,064 A * | 4/1991 | Grob et al. ....................... 60/276 |
| 5,157,340 A * | 10/1992 | Walton et al. .................. 324/641 |
| 5,309,213 A * | 5/1994 | Desjardins et al. ............. 356/70 |
| 5,332,961 A | 7/1994 | Hammerle |
| 5,438,420 A | 8/1995 | Harwick et al. |
| 5,497,099 A * | 3/1996 | Walton .......................... 324/641 |
| 6,079,251 A * | 6/2000 | Gaultier et al. ............... 73/23.31 |
| 6,148,089 A * | 11/2000 | Akino ........................... 381/356 |
| 6,253,601 B1 * | 7/2001 | Wang et al. ................. 73/114.55 |
| 6,366,353 B1 * | 4/2002 | Brown et al. .................. 356/318 |
| 6,391,267 B1 * | 5/2002 | Martin et al. .................. 422/173 |
| 6,634,210 B1 * | 10/2003 | Bosch et al. .................. 73/23.33 |
| 6,758,039 B2 * | 7/2004 | Kuboshima et al. ........... 60/311 |
| 6,809,820 B2 * | 10/2004 | Snelling et al. ............... 356/337 |
| 6,842,234 B2 * | 1/2005 | Kong et al. ..................... 356/70 |
| 6,862,927 B2 * | 3/2005 | Craig et al. .................. 73/114.69 |
| 6,891,383 B2 * | 5/2005 | Nicholson et al. ............ 324/698 |
| 7,157,919 B1 * | 1/2007 | Walton .......................... 324/641 |
| 7,355,415 B2 * | 4/2008 | Boyle et al. ................... 324/707 |
| 7,391,035 B2 * | 6/2008 | Kong et al. ................. 250/461.1 |

(Continued)

*Primary Examiner* — Helen Kwok
(74) *Attorney, Agent, or Firm* — Laurence A. Greenberg; Werner H. Stemer; Ralph E. Locher

(57) ABSTRACT

A method for determining a soot concentration in an engine oil of internal combustion engines, in which method a defined quantity of the engine oil is conducted with a defined flow speed along and/or through a measurement path. In a region of the measurement path, the engine oil is acted on with energy from at least one energy source in such a way that the soot particles contained in the engine oil at least partially absorb the energy. An energy quantity absorbed in the measurement path region is subsequently detected, and from this a soot concentration in the engine oil is determined. A device for determining the soot concentration in the engine oil of internal combustion engines is provided for performing the method.

21 Claims, 2 Drawing Sheets

(56) References Cited

U.S. PATENT DOCUMENTS

| | | | |
|---|---|---|---|
| 7,609,068 B2 * | 10/2009 | Ripley | 324/512 |
| 7,772,855 B2 * | 8/2010 | Sakuma et al. | 324/693 |
| 8,365,586 B2 * | 2/2013 | Ardanese et al. | 73/114.71 |
| 8,384,397 B2 * | 2/2013 | Bromberg et al. | 324/636 |
| 8,478,565 B2 * | 7/2013 | Ardanese et al. | 702/173 |
| 2005/0056083 A1 * | 3/2005 | Heremans et al. | 73/53.05 |
| 2009/0126458 A1 * | 5/2009 | Fleischer et al. | 73/28.01 |
| 2010/0055001 A1 * | 3/2010 | Ikeda et al. | 422/108 |
| 2010/0058832 A1 * | 3/2010 | Onishi et al. | 73/23.31 |
| 2010/0180668 A1 * | 7/2010 | Kruse et al. | 73/28.01 |
| 2011/0062973 A1 * | 3/2011 | Paterson | 324/693 |
| 2012/0102924 A1 * | 5/2012 | Ante et al. | 60/274 |

* cited by examiner

METHOD AND DEVICE FOR DETERMINING THE SOOT CONCENTRATION IN THE ENGINE OIL OF INTERNAL COMBUSTION ENGINES

CROSS-REFERENCE TO RELATED APPLICATION

This application claims the priority, under 35 U.S.C. §119, of German application DE 10 201 0 048 748.1, filed Oct. 16, 2010; the prior application is herewith incorporated by reference in its entirety.

BACKGROUND OF THE INVENTION

Field of the Invention

The invention relates to a method for determining the soot concentration in the engine oil of internal combustion engines. The invention also relates to a device for determining the soot concentration in the engine oil of internal combustion engines.

It is generally known that the introduction of soot into the engine oil of internal combustion engines can have an adverse effect on the oil properties. For example, an increased introduction of soot into the engine oil may cause a deterioration in the viscosity or lubrication capability of the engine oil. However, with the exhaust-gas aftertreatment requirements that are becoming ever more complex on account of modern exhaust-gas legislation, modern internal combustion engines are increasingly being operated at operating points in which an increased introduction of soot into the engine oil is unavoidable. Such an introduction of soot into the engine oil can therefore shorten the oil change intervals, which however opposes customer demand for ever longer oil change intervals.

There is therefore a need to be able to relatively precisely predict, in a functionally reliable manner, the introduction of soot into the engine oil of internal combustion engines, in particular of diesel internal combustion engines in utility vehicles, in order to be able to forecast the introduction of soot over the running time of the internal combustion engine for certain operating conditions.

U.S. Pat. No. 5,309,213 has already disclosed a method and a device by which the concentration of optically damping materials in liquids, for example soot in lubricating oil, can be determined. Specifically, it is proposed for this purpose that, in conjunction with a thin optical cell in the engine oil, light be coupled in and the optical damping at different locations be measured in this way.

SUMMARY OF THE INVENTION

It is accordingly an object of the invention to provide a method and a device for determining the soot concentration in the engine oil of internal combustion engines which overcome the above-mentioned disadvantages of the prior art devices of this general type, by which a soot concentration, and subsequently an introduction of soot, over a certain internal combustion engine running time can be determined in a simple and functionally reliable manner.

A method is proposed for determining the soot concentration in the engine oil of internal combustion engines, in which method a defined quantity of the engine oil conducted in the oil circuit is conducted with a defined flow speed along and/or through a measurement path. In a region of the measurement path, the engine oil is acted on with energy from at least one energy source in such a way that the soot particles contained in the engine oil at least partially absorb the energy. The energy quantity absorbed in the measurement path region is subsequently detected by at least one measurement device, preferably by at least one temperature measurement device, and the soot concentration in the engine oil is determined on the basis of the absorbed energy quantity.

By the method implementation according to the invention, therefore, a soot concentration is determined on the basis of the energy quantity absorbed in the engine oil, which permits a particularly dependable and functionally reliable determination of the soot concentration, and therefore subsequently of the introduction of soot into the engine oil.

There are basically different options for detecting the absorbed energy quantity by at least one measurement device. For example, the engine oil temperature detected preferably in an irradiation region by at least one temperature measurement device may be compared with a reference temperature, and from this the soot concentration in the engine oil may be determined. With such a design, a determination of the soot concentration may basically be carried out with one temperature measurement point, which may have one or else a plurality of temperature measurement devices. Such a temperature measurement point may for example be formed in the irradiation point or irradiation region of the energy source, or else also downstream of the irradiation point or irradiation region in the flow direction of the engine oil. Here, the reference temperature for the engine oil is determined under similar engine oil conditions but preferably without an introduction of energy by the energy source.

According to a particularly preferred specific method implementation, however, it is proposed that the engine oil in the region of the measurement path is acted on with energy between two temperature measurement points, which are spaced apart from one another in the flow direction, on the measurement path. A soot concentration in the engine oil is subsequently determined at least as a function of the engine oil temperature in the different regions of the measurement path, as detected by the temperature measurement points on the measurement path. With such a specific method implementation, particularly functionally reliable detection and evaluation of the introduction of energy into the engine oil is possible.

According to a further preferred method implementation, it may be provided that the flow speed of the engine oil in the region of the measurement path and/or the specific heat capacity of the engine oil and/or the absorption cross section of soot, for example in the form of the total effective cross section for the radiation absorption of the soot particles, are/is taken into consideration as further parameters for the determination of the soot concentration. The accuracy of the determination of the soot concentration can be increased yet further in this way.

Overall, it is therefore possible with such a method implementation according to the invention for the soot concentration in the engine oil to be dependably determined in a simple and functionally reliable manner, in particular determined as a function of defined operating points. Furthermore, it is alternatively or additionally also possible for catalytic converter operating points and/or regeneration measures for catalytic converters and/or particle filters to be determined in a simple manner.

The energy source is particularly preferably an optical energy source, for example a laser, for example a diode laser, which energy source irradiates energy in at least one defined irradiation point or region on the measurement path. In a preferred refinement of the present invention, it is provided that the measurement path is formed by a throughflow cuvette through which a defined quantity of the engine oil is conducted, wherein it is preferably provided that the temperature measurement points are arranged in the region of cuvette regions which are spaced apart from one another. The temperature detection then takes place here preferably in such a way that, for example by a differential temperature determination, the temperature difference upstream and downstream of the irradiation point or region on the measurement path is determined and evaluated. For this purpose, the energy source then irradiates energy into the engine oil preferably in the region between the two temperature measurement points which are spaced apart from one another.

It is basically to be assumed that the laser beam which radiates all the way through the oil volume perpendicular to the flow direction causes a uniform introduction of energy over the entire cross-sectional area of the oil volume in the irradiation point, wherein the energy is absorbed by the soot particles substantially uniformly in relation to the cross-sectional area. The energy is subsequently dissipated directly to the engine oil causing an increase, uniform in relation to the cross-sectional area, in the engine oil temperature, such that the use of one sensor for temperature detection at the at least one temperature measurement point, in particular at a temperature measurement point situated in the region of or downstream of the irradiation point, is sufficient. In particular if relatively high soot concentrations are to be expected at which the laser beam possibly no longer radiates or can no longer radiate all the way through the oil volume because the soot particles already prematurely absorb the energy, it has however proven to be advantageous for a plurality of temperature sensors to be arranged spaced apart from one another in the region of the at least one temperature measurement point, by which temperature sensors a possibly spatially varying temperature distribution in the engine oil, for example in the region of or downstream of the irradiation point or region, can be detected in a simple and reliable manner. For this purpose, the temperature sensors are arranged preferably in the same cross-sectional plane in relation to the flow direction of the engine oil and/or the temperature sensors are at substantially the same distance from the irradiation region in the flow direction.

In a further alternative solution, it may be provided that an engine oil temperature in the irradiation point or region is detected by a temperature measurement device, wherein it is preferably provided that the engine oil temperature upstream of the irradiation point or region is detected at a first temperature measurement point and an engine oil temperature in the irradiation point or region is detected at a second, spaced apart temperature measurement point. It is particularly preferable here, according to one embodiment, for the temperature measurement device to be formed by a pyrometer by which thermal radiation emitted by the engine oil in the irradiation point or region is detected, and subsequently a soot concentration in the engine oil is determined. In this way, the oil temperature is now detected directly at the irradiation point by a pyrometer. This utilizes the fact that, if the radiation penetration depth of the energy source decreases, only a smaller oil volume is heated than would be heated with the same amount of energy and a greater radiation penetration depth. In this way, the smaller oil volume is heated more intensely, such that as a result, the oil volume also emits more thermal radiation which can ultimately be measured by the pyrometer.

A method implementation is particularly preferred in which the soot concentration is detected continuously or at intervals, for example periodically, over the operating duration for defined operating states of the internal combustion engine and is transmitted to an evaluation device in which a service-life-dependent and/or load-dependent or operating-point-dependent introduction of soot into the engine oil is determined. With a soot concentration determined in this way, it is possible in a simple manner to determine when an oil change is possibly to be expected. If appropriate, an operating strategy of the internal combustion engine may then be adjusted or influenced such that an oil change will be necessary at a defined point in time.

A device, which forms a sensor, for determining the soot concentration in the engine oil of internal combustion engines is proposed, which device preferably has a throughflow cuvette for forming a measurement path. Furthermore, the device has one or more, in particular two temperature measurement point(s) spaced apart from one another in the region of the measurement path. Furthermore, at least one energy source is provided by which energy can be supplied to the soot particles in the engine oil in at least one defined irradiation point or region. Finally, the device according to the invention contains an evaluation device to which at least the temperature detected at the at least one temperature measurement point can be supplied for the determination of the soot concentration. The parameters required for the determination of the introduction of soot, aside from the temperature data to be detected in each case, may be fixedly predefined in the system.

The advantages obtained with a device of the type have already been discussed in detail above.

In a specific refinement, the temperature measurement points may contain in each case at least one temperature sensor formed by a coil, which temperature sensors are constituent parts of a bridge circuit which can be calibrated for temperature detection and which has resistors, wherein the coils are arranged spaced apart from one another in the region of the throughflow cuvette which forms the measurement path.

Other features which are considered as characteristic for the invention are set forth in the appended claims.

Although the invention is illustrated and described herein as embodied in a method and a device for determining the soot concentration in the engine oil of internal combustion engines, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
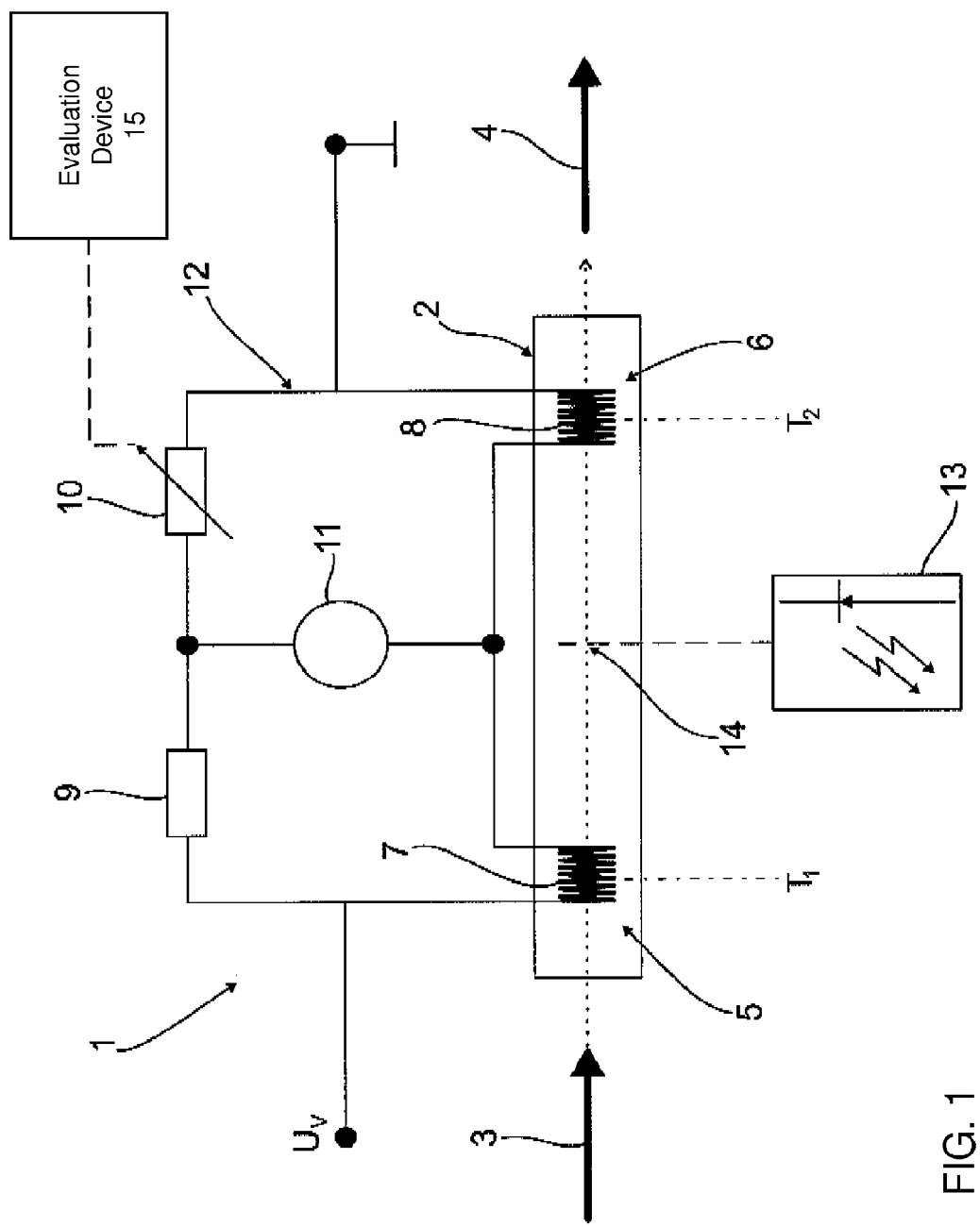
FIG. 1 is an illustration showing an exemplary embodiment of a device for determining the introduction of soot into engine oil according to the invention.

Referring now to the figures of the drawing in detail and first, particularly, to FIG. 1 thereof, there is shown a sensor 1 for determining a soot concentration in an engine oil of an internal combustion engine, which sensor 1 has a throughflow cuvette 2 which has a defined, predetermined volume. A predefined amount of the engine oil of the internal combustion engine flows through the through flow cuvette 2 in a direction of flow arrows 3, 4 for a determined time period, wherein the throughflow speed of the engine oil through the throughflow cuvette 2 is substantially always constant and has a predefined and therefore known speed value.

Here, by way of example, a first wire coil 7 is arranged in the flow path of the engine oil in an inflow-side cuvette region 5. Arranged in an outflow-side cuvette region 6 and spaced apart from the first wire coil is a further, substantially structurally identical wire coil 8 which likewise lies in the flow path of the engine oil.

The two coils 7, 8 together with resistors 9, 10, of which the resistor 10 is configured as a variable resistor, and with a voltage measurement unit 11 form a bridge circuit 12 such as is known per se, which bridge circuit is illustrated here merely by way of example and schematically and may self-evidently also be of any other suitable design.

With the bridge circuit 12 of this type, two temperature measurement points or sensors are formed spaced apart from one another in the region of the coils 7, 8, by which temperature measurement points or sensors the temperatures of the engine oil in the inflow-side cuvette region 5 and in the outflow-side cuvette region 6 can be detected. Specifically, in the case of the bridge circuit 12 selected and shown here, the temperature dependency of the electrical resistance of conductors is utilized for the measurement of the temperature. This is generally known and need not be explained in any more detail at this juncture.

The sensor 1 also contains, as an optical energy source, a diode laser 13 which is selected by way of example here and by which, as is illustrated merely by dashed lines in FIG. 1, optical energy is irradiated into the throughflow cuvette 2 in the region between the two temperature measurement points formed by the wire coils 7, 8, in such a way that the soot particles contained in the engine oil absorb the energy and subsequently dissipate the energy back to the engine oil, causing an increase in the engine oil temperature. In this way, in the region of the wire coil 8, a temperature $T_2$ is measured which is greater to a defined extent than the temperature $T_1$ detected and measured in the region of the wire coil 7. On the basis of the temperature difference between the two temperatures $T_2$ and $T_1$ at the temperature measurement points at the wire coils, it is possible to determine the respective soot concentration in the engine oil for the present operating state of the internal combustion engine, and to correspondingly determine a total introduction of soot in an operating-point-dependent manner and/or over the service life of the internal combustion engine, by an evaluation device 15, illustrated here merely highly schematically, in conjunction with the known flow speed of the engine oil in the cuvette region, the specific heat capacity of the engine oil used and the known absorption cross section of soot or of the soot particles.

The central positioning of an irradiation point 14 in relation to the position of the wire coils 7, 8 which form the temperature measurement points is selected merely by way of example and arbitrarily here. Other arrangements are self-evidently also by all means possible.

Figure 2:
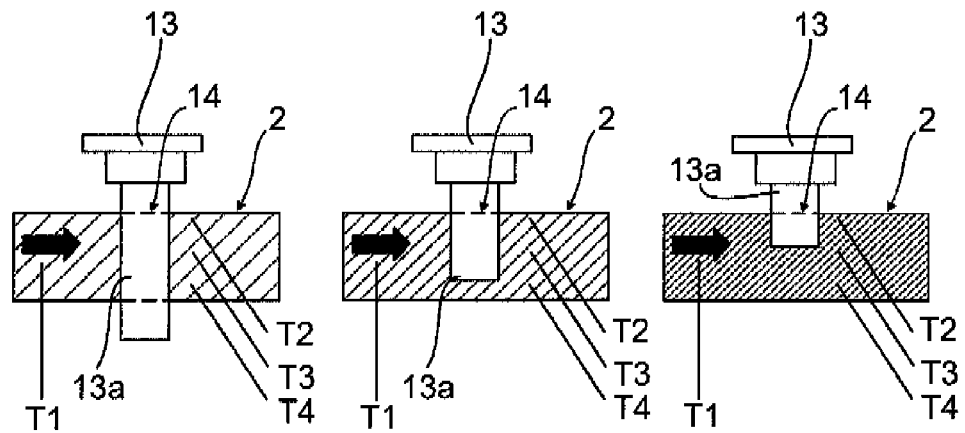
FIG. 2 is an illustration showing a construction having a plurality of temperature sensors arranged downstream of an irradiation point.

Finally, FIG. 2 merely highly schematically illustrates an alternative embodiment in which only one temperature sensor, formed for example by a coil, is provided upstream of the irradiation point 14, which temperature sensor detects the temperature $T_1$, whereas in this case for example three temperature sensors are arranged spaced apart from one another downstream of the irradiation point 14, which temperature sensors, in relation to a certain cuvette cross section situated in the flow direction, detect the temperatures $T_2$, $T_3$ and $T_4$ at different points of the cross section downstream of the irradiation point 14, whereby it is possible to detect a spatial distribution of the engine oil temperatures, as viewed over the flow cross section, downstream of the irradiation point 14.

In the situation, illustrated in the left-hand image of FIG. 2, that only a normal soot concentration is present in the engine oil, the laser beam 13a radiates through the entire measurement path or cuvette region, such that in the region downstream of the irradiation point 14, the temperatures $T_2$, $T_3$ and $T_4$ each have substantially the same temperature value.

In contrast, if the soot concentration in the engine oil increases such that the laser beam 13a can no longer penetrate all the way through the measurement path region, as illustrated in the middle image of FIG. 2, different temperature values are determined in the region downstream of the irradiation point 14 for the temperatures $T_2$ and $T_3$ on the one hand and $T_4$ on the other hand, that is to say that, in the example shown here, no temperature increase or only an insignificant temperature increase occurs in the region of the position of the temperature sensor which measures the temperature $T_4$ in relation to the temperature $T_1$ measured upstream.

The same is illustrated in the right-hand image of FIG. 2 for a yet higher soot content in the engine oil. In this case, no deviation or only an insignificant deviation of the temperature value in relation to the temperature $T_1$ is detected in the region of the temperature sensors which detect the temperatures $T_3$ and $T_4$.

On the basis of the non-uniform spatial distribution of the temperature in relation to a flow cross section situated perpendicular to the flow direction, it is therefore possible, if appropriate taking into consideration the parameters already described above or at least one of the parameters, to draw conclusions regarding the soot content in the oil. Here, the temperature sensors (not illustrated here) which detect the temperatures $T_2$, $T_3$ and $T_4$ lie preferably approximately in the same cross-sectional plane through the measurement path 2.

Figure 3:
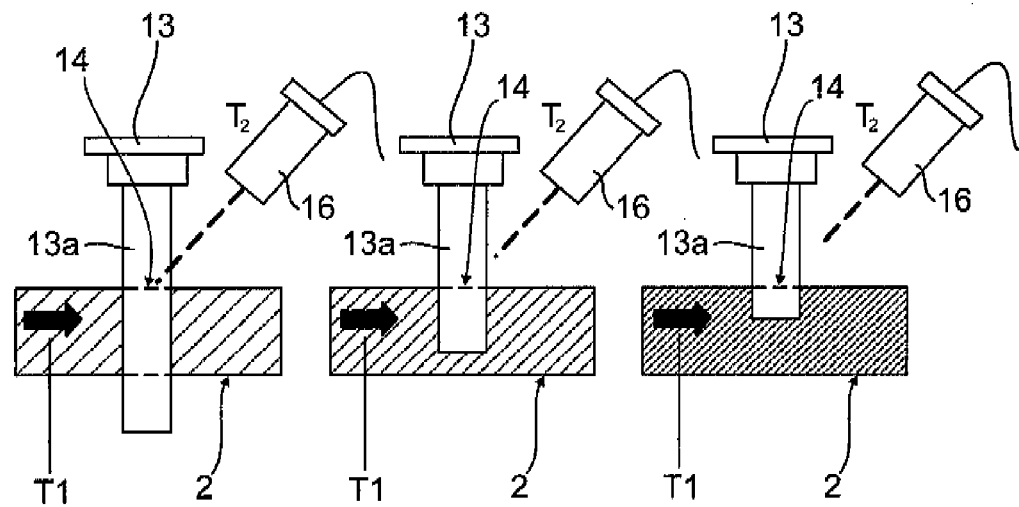
FIG. 3 is an illustration showing a further alternative variant of the device according to the invention.

FIG. 3 shows the same situation with regard to the soot concentration, but in FIG. 3, in contrast to the embodiment of FIG. 2, there is not a plurality of temperature sensors formed for example by coils and arranged spaced apart from one another downstream of the irradiation point 14, but rather the oil temperature $T_2$ is measured directly at the irradiation point 14 by a pyrometer 16. If the radiation penetration depth of the laser beam 13a decreases, as shown from the left to the right in the images of FIG. 3, a smaller oil volume is heated by the same amount of energy, which smaller oil volume is however heated more intensely and therefore, as a result, also dissipates a greater amount of thermal radiation, which can then be measured by the pyrometer 16. In this way, conclusions can be drawn regarding the soot content in the oil.

It is self-evident that, in the above examples described with regard to FIGS. 2 and 3, the temperature sensors at the respective temperature measurement points may be formed in each case in different ways, for example by the coils shown in conjunction with FIG. 1, or else by suitable other temperature sensors such as are known to a person skilled in the art.

The invention claimed is:

1. A method for determining a soot concentration in an engine oil of an internal combustion engine, which comprises the steps of:

conducting a defined quantity of the engine oil with a defined flow speed along or through a measurement path;

in a region of the measurement path, acting on the engine oil with energy from at least one energy source such that soot particles contained in the engine oil at least partially absorb the energy;

detecting an energy quantity absorbed in the measurement path region by at least one measurement device; and determining the soot concentration in the engine oil from analyzing the energy quantity absorbed;

with a temperature sensor, detecting a temperature upstream of an irradiation region; and with a plurality of temperature sensors disposed in a cross-sectional plane downstream of the irradiation region, detecting a plurality of temperatures at different locations of the cross-sectional plane such that a spatially varying temperature distribution seen over a flow cross-section of the engine oil is detectable downstream of the irradiation region.

2. The method according to claim 1, which further comprises:

providing the at least one measurement device as at least one temperature measurement device;

detecting an engine oil temperature in the irradiation region with the at least one temperature measurement device;

comparing the engine oil temperature with a reference temperature; and determining the soot concentration in the engine oil from results of the comparing step, the reference temperature for the engine oil is determined under similar engine oil conditions but without an introduction of energy by the energy source.

3. The method according to claim 1, which further comprises acting on the engine oil in a region of the measurement path with the energy between two temperature measurement points, which are spaced apart from one another in a flow direction, on the measurement path, and the soot concentration in the engine oil is determined from the engine oil temperature in different regions of the measurement path, as detected by means of the temperature measurement points on the measurement path.

4. The method according to claim 1, wherein at least one of a flow speed of the engine oil in a region of the measurement path, a specific heat capacity of the engine oil, or an absorption cross section of the soot is taken into consideration as further parameters for a determination of the soot concentration.

5. The method according to claim 1, which further comprises providing an optical energy source as the energy source which irradiates energy in at least one defined irradiation point or region on the measurement path.

6. The method according to claim 1, which further comprises forming the measurement path using a throughflow cuvette through which the defined quantity of the engine oil is conducted, and a plurality of temperature measurement points are disposed in a region of cuvette regions which are spaced apart from one another.

7. The method according to claim 6, wherein the energy source irradiates in the region between two temperature measurement points which are spaced apart from one another, such that an engine oil temperature measurement takes place in a region upstream and downstream of an irradiation region.

8. The method according to claim 7, which further comprises disposing the plurality of temperature sensors spaced apart from one another in a region of at least one temperature measurement point, by means of the temperature sensors a possibly spatially varying temperature distribution in the engine oil, in a region of or downstream of the irradiation region, is detected, wherein the temperature sensors are disposed in a same cross-sectional plane in relation to a flow direction of the engine oil and/or are substantially a same distance from the irradiation region in the flow direction.

9. The method according to claim 1, which further comprises detecting an engine oil temperature in an irradiation region by a temperature measurement device.

10. The method according to claim 9, which further comprises:

forming the temperature measurement device as a pyrometer by means of which thermal radiation emitted by the engine oil in the irradiation region is detected; and determining the soot concentration in the engine oil on a basis of detected thermal radiation.

11. The method according to claim 1, which further comprises:

detecting the soot concentration one of continuously or at intervals over an operating duration for defined operating states of the internal combustion engine; and transmitting soot concentration values to an evaluation device in which at least one of a service-life-dependent or a load-dependent introduction of the soot into the engine oil is determined.

12. The method according to claim 1, wherein the measurement device is a temperature measurement device.

13. The method according to claim 5, which further comprises providing a laser as the optical energy source.

14. The method according to claim 8, which further comprises disposing the plurality of temperature sensors spaced apart from one another in a region of a temperature measurement point situated downstream of the irradiation region.

15. The method according to claim 1, which further comprises detecting an engine oil temperature upstream of an irradiation region at a first temperature measurement point and an further engine oil temperature in the irradiation region at a second, spaced apart temperature measurement point.

16. A device for determining a soot concentration in an engine oil of an internal combustion engine, the device comprising:

a measurement path defining at least one temperature measurement point;

at least one energy source by means of which energy can be supplied to soot particles in the engine oil in at least one defined irradiation region; and an evaluation device to which at least a temperature detected at the at least one temperature measurement point can be supplied for a determination of the soot concentration in the engine oil;

a temperature sensor disposed for detecting a temperature upstream of the irradiation region; and a plurality of temperature sensors disposed in a cross-sectional plane downstream of the irradiation region for detecting a plurality of temperatures at different locations of the cross-sectional plane such that a spatially varying temperature distribution seen over a flow cross-section of the engine oil is detectable downstream of the irradiation region.

17. The device according to claim 16, wherein said measurement path is a throughflow cuvette and said at least one temperature measurement point is one of two temperature measurement points which are disposed spaced apart from one another in a region of said throughflow cuvette.

18. The device according to claim 16, wherein said energy source is an optical energy source.

19. The device according to claim 17, further comprising a bridge circuit containing at least one temperature sensor associated with said at least one temperature measurement point, said at least one temperature sensor having a coil and is a constituent part of said bridge circuit which can be calibrated for temperature detection and having resistors.

20. The device according to claim 16, wherein said energy source is a diode laser.

21. The device according to claim 19, wherein said coil is one of a plurality of coils spaced apart from one another in a region of said throughflow cuvette.

* * * * *